US009132171B2

(12) United States Patent
Goel et al.

(10) Patent No.: US 9,132,171 B2
(45) Date of Patent: Sep. 15, 2015

(54) TEST OF INSULIN AS A DRUG TO REDUCE RESTENOSIS OF VESSELS

(71) Applicant: WISCONSIN ALUMNI RESEARCH FOUNDATION, Madison, WI (US)

(72) Inventors: Shakti Goel, Madison, WI (US); Lian Guo, Madison, WI (US); K. Craig Kent, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/795,235

(22) Filed: Mar. 12, 2013

(65) Prior Publication Data

US 2013/0330376 A1 Dec. 12, 2013

Related U.S. Application Data

(60) Provisional application No. 61/650,695, filed on May 23, 2012.

(51) Int. Cl.
| | | |
|---|---|---|
| *A61K 38/28* | (2006.01) | |
| *A61K 38/18* | (2006.01) | |
| *A61K 38/00* | (2006.01) | |
| *A61K 38/16* | (2006.01) | |
| *C07K 1/00* | (2006.01) | |
| *A61K 9/00* | (2006.01) | |
| *A61K 31/28* | (2006.01) | |
| *A61L 31/16* | (2006.01) | |
| *A61L 31/14* | (2006.01) | |

(52) U.S. Cl.
CPC . *A61K 38/28* (2013.01); *A61K 9/00* (2013.01); *A61K 31/28* (2013.01); *A61K 38/18* (2013.01); *A61L 31/145* (2013.01); *A61L 31/16* (2013.01); *A61L 2300/414* (2013.01); *A61L 2300/43* (2013.01)

(58) Field of Classification Search
None
See application file for complete search history.

(56) References Cited

U.S. PATENT DOCUMENTS

| 5,352,240 | A | | 10/1994 | Ross |
| 5,591,709 | A | * | 1/1997 | Lindenbaum ............... 514/6.5 |
| 5,624,837 | A | | 4/1997 | Fodor et al. |
| 5,627,264 | A | | 5/1997 | Fodor et al. |
| 5,705,732 | A | | 1/1998 | Sims et al. |
| 5,807,743 | A | | 9/1998 | Stinchcomb et al. |
| 5,847,082 | A | | 12/1998 | Rother et al. |
| 5,853,722 | A | | 12/1998 | Rollins et al. |
| 6,464,983 | B1 | * | 10/2002 | Grotendorst ............... 424/198.1 |
| 6,797,000 | B2 | | 9/2004 | Simpson et al. |
| 7,008,773 | B1 | | 3/2006 | Freyberg et al. |
| 7,323,323 | B2 | | 1/2008 | Elliott et al. |
| 7,780,993 | B2 | | 8/2010 | Reisner et al. |
| 8,067,031 | B2 | | 11/2011 | Daniloff et al. |
| 8,252,283 | B2 | | 8/2012 | Freyberg et al. |
| 2003/0180300 | A1 | | 9/2003 | Grotendorst |
| 2007/0128175 | A1 | | 6/2007 | Ozbas et al. |
| 2009/0186069 | A1 | * | 7/2009 | DeYoung et al. ............ 424/426 |

OTHER PUBLICATIONS

Wound Dressings, DermNetZ, 2009, downloaded Feb. 14, 2014).*
Lee et al 2010. J. Clin. Invest. 120:3340-3349.*
Liu et al. 2007. Biotech. Appl. Biochem. 47:105-112.*
Blom, et al., In Vitro Evidence for Differential Involvement of CTGF, TGFB, and PDGF-BB in Mesangial Response to Injury, Nephrology Dialysis Transplantation, 2001, 16:1139-1148.
Breen, et al., Insulin Increases Reendothelialization and Inhibits Cell Migration and Neointimal Growth After Arterial Injury, Arterioscler. Thromb. Vasc. Biol., 2009, 29:1060-1066.
Gore-Hyer, et al., Selective Stimulation of Collagen Synthesis in the Presence of Costimulatory Insulin Signaling by Connective Tissue Growth Factor in Scleroderma Fibroblasts, Arthritis & Rheumatism, 2003, 48(3):798-806.
Grotendorst, et al., Combinatorial Signaling Pathways Determine Fibroblast Proliferation and Myofibroblast Differentiation, FASEB J., 2004, 18:469-479.
Grotendorst, et al., Individual Domains of Connective Tissue Growth Factor Regulate Fibroblast Proliferation and Myofibroblast Differentiation, FASEB J., 2005, 19:729-738.
Johns Hopkins, Heart Health Special Report, Surgery for Heart Disease: Angioplasty vs. Bypass Surgery, Posted in Heart Health on Nov. 16, 2007, 3 pages.
Kanjickal, et al., Polymeric Sustained Local Drug Delivery System for the Prevention of Vascular Intimal Hyperplasia, Journal of Biomedical Materials Research Part A, 2004, 68A(3):489-495.
Kundi, et al., Arterial Gene Transfer of the TFG-B Signalling Protein Smad3 Induces Adaptive Remodelling Following Angioplasty: A Role for CTGF, Cardiovascular Research, 2009, 84:326-335.
Lindner, et al., Differential Expression of Matrix Metalloproteases in Human Fibroblasts with Different Origins, Biochemistry Research International, vol. 2012, Article ID 875742, 10 pages.
Pagano, et al., Localization of a Constitutively Active, Phagocyte-Like NADPH Oxidase in Rabbit Aortic Adventitia: Enhancement by Angiotensin II, Proc. Natl. Acad. Sci. USA, 1997, 94:14483-14488.
Ryan, et al., Transforming Growth Factor-Beta-Dependent Events in Vascular Remodeling Following Arterial Injury, J. Vasc. Res., 2003, 40:37-46.
Ryer, et al., PKC* Is Necessary for Smad3 Expression and Transforming Growth Factor B-Induced Fibronectin Synthesis in Vascular Smooth Muscle Cells, Arterioscler. Thromb. Vasc. Biol., 2006, 26:780-786.
Schantz, et al., Standardized Assay for Clostridium Botulinum Toxins, Journal of the Association of Official Analytical Chemists, 1978, 61(1):96-99.
Seher, et al., Gene Expression Profiling of Connective Tissue Growth Factor (CTGF) Stimulated Primary Human Tenon Fibroblasts Reveals an Inflammatory and Wound Healing Response in Vitro, Molecular Vision, 2011, 17:53-62.
Skalsky, et al., A Perivascular System Releasing Sirolimus Prevented Intimal Hyperplasia in a Rabbit Model in a Medium-Term Study, International Journal of Pharmaceutics, 2012, 427:311-319.
U.S. National Institutes of Health, Clinical Trial NCT00157716, Oct. 30, 2006, 3 pages.

* cited by examiner

*Primary Examiner* — Shulamith H Shafer
(74) *Attorney, Agent, or Firm* — Quarles & Brady LLP

(57) ABSTRACT

Methods, compositions, and devices for treating restenosis are described. In accord with the invention, a composition containing CTGF and insulin is applied to blood vessels and restenosis is reduced or prevented.

12 Claims, 8 Drawing Sheets

Col III

Col I

TEST OF INSULIN AS A DRUG TO REDUCE RESTENOSIS OF VESSELS

CROSS-REFERENCE TO RELATED APPLICATIONS

This application claims the benefit of U.S. Provisional Application No. 61/650,695, filed on May 23, 2012, which is incorporated by reference herein in its entirety.

STATEMENT REGARDING FEDERALLY SPONSORED RESEARCH OR DEVELOPMENT

This invention was made with government support under HL068673 awarded by the National Institutes of Health. The government has certain rights in the invention.

BACKGROUND

Atherosclerosis, the leading cause of death in the United States, is currently addressed through several treatment modalities, including angioplasty, endarterectomy, and bypass. When a vessel is injured during angioplasty or bypass graft surgery, the injury can induce a physiological response that becomes evident 3-6 months later whereby the vessels are further narrowed ("restenosis"). Restenosis involves (i) intimal cell hyperplasia (growth of inner vessel lining), and (ii) constrictive vessel wall remodeling. Neo-intimal thickening can be accompanied by compensatory enlargement of the vessel wall, which can be measured by changes in external elastic lamina area. This growth, termed adaptive remodeling, which prevents the neo-intimal lesion from impinging on the lumen, is triggered by the activation of smooth muscle cells (SMCs) lining the arterial walls. Restenosis occurs in 30-50% of the 2 million patients who undergo this surgery every year.

Currently, restenosis is treated by rapamycin provided through stents. Unfortunately, stents increase fibrosis and intima thickening and do not allow vessels to expand. Stents also prevent healing of the endothelial layer, causing thrombosis. Rapamycin interferes with re-endothelization, which is required for proper vessel healing. Further, rapamycin provided via stent is susceptible to rapid dilution by the bloodstream. Systemic treatments, which cannot be targeted to the site of restenosis, are generally very limited.

Vessel walls are primarily composed of collagen types I (rigid) and III (elastic). Connective Tissue Growth Factor (CTGF), a soluble factor secreted by blood vessel adventitial cells, activates smooth muscle in the vessel causing increased adaptive remodeling of the vessel (Kundi et al., Cardiovascular Research 84:326-335, 2009). In a laboratory model of restenosis, the lumen of balloon-injured blood vessels was expansively remodeled when CTGF was applied (Kundi et al., 2009). However, CTGF alone is not sufficient to treat restenosis, at least because it neither suppresses neo-intimal growth nor vessel constriction.

CTGF induces collagen synthesis (see U.S. Patent Publication No. 2003/0180300). The combination of insulin (10 ng/ml) and CTGF (2.5 ng/ml) stimulates total collagen synthesis in dermal fibroblasts isolated from patients with scleroderma/systemic sclerosis (Gore-Hyer et al., Arthritis and Rheumatism 48:798-806, 2003). Normal rat kidney (NRK) fibroblasts stimulated with TGFbeta or CTGF in the presence of IGF-2 responded by differentiating into myofibroblasts and increasing both collagen type I and collagen type III synthesis, with no indication that collagen III levels increased significantly relative to collagen I levels (Grotendorst et al., FASEB 18:469-479, 2004). Further, the combination of CTGF and IGF-2 had no significant effect on cell proliferation or collagen synthesis in human Tenon's fibroblasts (Seher et al., Mol. Vision 17:53-62, 2011).

Previous work suggests that insulin can be used to increase re-endothelialization in vessels and to inhibit cell migration into the intima (Breen et al., Arterioscler. Thromb. Vasc. Biol. 29:1060-1066, 2009). However, insulin does not decrease intima cell proliferation or apoptosis (Breen, et al., 2009), and evidence suggests that insulin stimulates adaptive remodeling of injured vessels.

There has arisen in the art a need for an anti-restenosis agent. Preferably, an anti-restenosis agent could preserve vessel lumen size by suppressing both neo-intimal growth and vessel constriction and also enhance adaptive remodeling in injured vessels.

SUMMARY OF THE INVENTION

The invention relates generally to methods of treating restenosis, and more particularly to a composition for treating restenosis, the composition comprising insulin and connective tissue growth factor (CTGF).

In a first aspect, the present invention is summarized as a method of preventing restenosis. The method includes the steps of applying to an injured vessel a composition comprising connective tissue growth factor (CTGF) and insulin, wherein the composition suppresses neo-intimal growth and increases adaptive remodeling in the vessel relative to an injured vessel that is not treated with the composition. In some embodiments the composition is applied via a wrap that supports the composition.

In a second aspect, the present invention is summarized as a wrap for providing a composition of the invention to treat, reduce, or prevent restenosis. In some embodiments the wrap includes a substrate and a composition supported on the substrate. In some embodiments the wrap is a perivascular wrap. In some embodiments, the wrap includes a polymeric material or a hydrogel material.

In a third aspect, the present invention is summarized as a composition that contains CTGF and insulin.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 3 depicts direct ELISA showing relative collagen III (dark) and I (light) when respective conditioned medium is added to rat fibroblasts 72 hours after treatment ($*p<0.05$).

Figure 1:
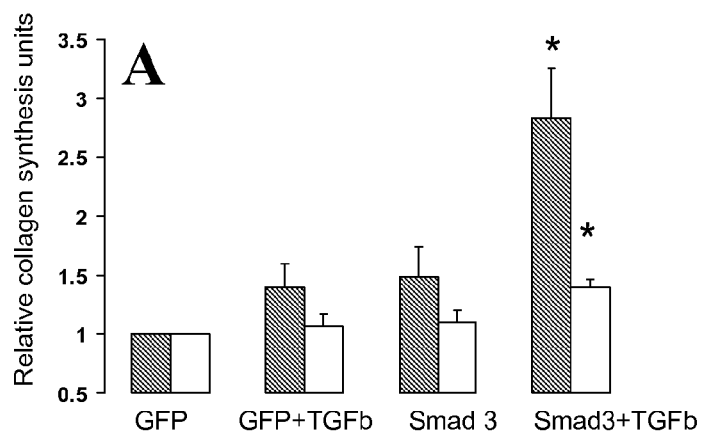
FIGS. 1A-B illustrates increased collagen III production relative to collagen I production in TGF-beta/Smad3-stimulated fibroblasts. (A) Direct ELISA depicting collagen III (dark) and collagen I (light) in culture medium obtained from rat aortic fibroblasts treated for 72 hours with various conditioned media (x-axis) derived from SMCs (*p<0.05). (B) Western Blot depicting collagen III and I synthesis in culture media obtained from the treatments described in part A of FIG. 1.
Figure 1:
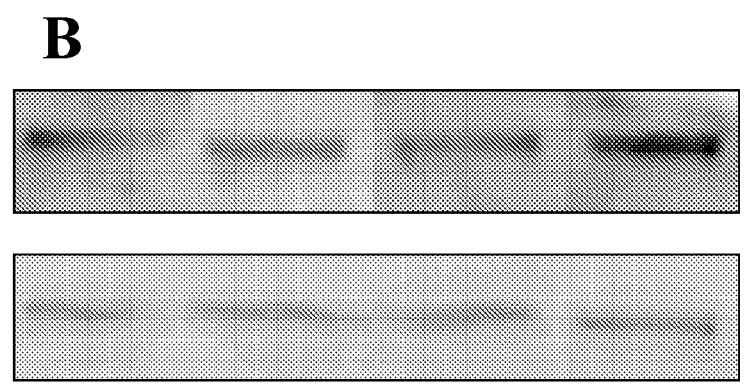

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE INVENTION

The present invention relates to the inventors' observation, previously unknown, that combinations of CTGF and IGF-2 and combinations of CTGF and insulin synergistically increase levels of collagen III expression relative to collagen I expression in aortic fibroblast cells. Although CTGF and IGF-2 were both known to increase total collagen expression in non-aortic fibroblast cells, prior to the inventors' experiments no evidence would have suggested to a skilled artisan i) that combinations of CTGF and IGF-2 and combinations of CTGF and insulin could synergistically increase levels of collagen in fibroblasts, let alone in aortic fibroblasts, or ii) that combinations of CTGF and IGF-2 and combinations of CTGF and insulin could synergistically increase levels of expression of collagen III relative to collagen I.

The ratio of collagen III:I synthesis is important in terms of preventing restenosis. Collagen type I is thought to increase restrictive remodeling (Sarah T. Ryana, Victor E. Kotelianskya, Philip J. Gotwalsa, Volkhard Lindnerb. Transforming Growth Factor-Beta-Dependent Events in Vascular Remodeling following Arterial Injury. J Vasc Res 2003; 40:37-46), which could counter efforts to prevent restenosis.

The inventors predicted that a preferred anti-restenosis agent would be one that could preserve vessel lumen size by suppressing both neo-intimal growth and vessel constriction and also enhance adaptive remodeling in vessels. To develop such an agent, the inventors treated rat aortic cells with combinations of CTGF and IGF-2 or insulin and measured subsequent synthesis of collagen types I and III. CTGF and insulin alone induced some increase in collagen III in rat aortic cells. However, the combination of CTGF and insulin resulted in a significant synergistic increase in collagen III in rat aortic cells.

To test the combination in vivo, male rats underwent left carotid artery balloon angioplasty. Immediately following catheter removal, a combination of CTGF and insulin suspended in a Pluronic® gel was applied to the outside of the arterial wall. After 14 days the animals were sacrificed and carotid artery preparations were made. The rat vessels showed an enlarged lumen area, increased external elastic lamina and decreased neointimal growth.

It is contemplated that the data derived from the rat model system described in the Examples Section is applicable to the corresponding condition in a human. The methods and formulations of the present invention are useful for treating or preventing restenosis in humans. The success of methods employing the formulations of the inventions can be monitored by measuring lumen area, vessel size, and blood flow, which can be monitored using intravascular ultrasound or angiography. Also, decrease in ischaemic symptoms and reduced hospital visits by patients are useful clinical indicators of success.

In one embodiment, the composition comprising insulin and CTGF can be used to prevent restenosis. Advantageously, the composition of the present invention can be applied to the external surface of a vessel at the site of surgical injury, e.g., via a wrap or patch such as a perivascular wrap or patch. The patch or wrap can include a cytocompatible and biocompatible substrate that supports or contains the composition or composition for application to the site of vessel injury. Patches and wraps suited for use with the composition are known in the art (e.g., Skalsky et al., Int. J. Pharmaceu. 427:311,319, 2012 and Kanjickal et al., J. Biomed. Mater. Res. A. 68:489-495, 2004). A cytocompatible substrate is not cytotoxic to desired cells. A biocompatible substrate does not cause a significant immunological and inflammatory response when placed at the dermal wound and preferably biodegrades into non-toxic species.

In some embodiments, the substrate includes a hydrogel. Hydrogels useful in the present invention include, in general, naturally-derived hydrogels, semi-synthetic hydrogels and synthetic hydrogels. A particularly preferred hydrogel for use as a support substrate is a semi-synthetic derivative of hyaluronic acid which is sold under the tradename EXTRACEL (Glycosan Biosystems). An alternative hydrogel useful in the invention is available under the federally registered trademark HYAFF (Fidia Advanced Biopolymer s.r.l.). HYAFF materials are available in the form of fibers, membranes, microspheres and three dimensional matrices. Besides being non-cytotoxic and biocompatible, HYAFF is also biodegradable. Synthetic hydrogels include materials described in U.S. Published Patent Application 2007/0128175, incorporated herein by reference as if set forth in its entirety, directed to the use of small peptides as gel scaffold building blocks via self-assembly hydrogelation. Common components of semi-synthetic or synthetic hydrogels include, e.g., polyvinyl alcohol, sodium polyacrylate, acrylate polymers and copolymers with an abundance of hydrophilic groups. Natural hydrogel materials include, e.g., agarose, methylcellulose, collagen, and hyaluronic acid (also termed hyaluronan or hyaluronate).

In other embodiments, the substrate may be made of a polymeric material. Useful polymeric materials for this purpose include, but are not limited to, polytetrafluoroethylene, polydimethylsiloxane, poly-vinylidine fluoride, polyethylene, polystyrene, polycarbonate, polyhydroxyethyl methacrylate, polyvinyl alcohol, polyvinyl chloride, polycaproamide, polyetheyleneoxide, polyethyleneterephthalate, polyacrylonitrile, silicones, polysilanes, polysiloxanes, polyurethanes, polylactides, polyglycolic acid, polybeta hydroxybutyrate, polyepisilon caprolactone, polyanhyhdrides, polyorthoesters, polyiminocarbonates, mixtures thereof and copolymers thereof. In certain embodiments, the support substrate includes an interpenetrating polymer network ("IPN") of at least two polymeric materials.

In a preferred embodiment of the invention, the composition is applied outside the blood vessel at the site of surgery during the surgical procedure. Surgeries that could benefit from use of the method and composition of the present invention include, but are not limited to, coronary artery bypass, endarterectomy, vein grafting, surgery performed to treat peripheral vascular diseases or Raynaud's phenomenon and organ transplant surgeries. In the United States alone, it is estimated that over 700,000 annual coronary artery bypass grafts are performed (U.S. Clinical Trial NCT00157716, Oct. 30, 2006), making the invention particularly useful.

It is contemplated that the compositions and methods of the present invention could be useful for treating diabetic patients in need of both insulin and bypass graft surgery. Many diabetic patients with triple vessel disorder (atherosclerosis) are required to undergo bypass graft rather than angioplasty. (Johns Hopkins Health Alerts, Heart Health Special Report, "Surgery for heart disease: angioplasty vs. bypass surgery," Nov. 16, 2007). The composition and patch/wrap could be used to prevent restenosis in diabetic patients and provide diabetic patients with needed insulin.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

As used herein, "about" means within 5% of a stated concentration range or within 5% of a stated time frame.

As used herein, "effective amount" means an amount of an agent sufficient to evoke a specified physiological effect according to the present invention.

The invention will be more fully understood upon consideration of the following non-limiting Examples. All papers and patents disclosed herein are incorporated herein by reference as if set forth in their entirety.

EXAMPLES

Example 1

Materials and Methods

Cell Culture. Aortic SMCs were isolated from mouse (MOVAS) aortas. Rat aortic fibroblasts were isolated as previously described by Pagano et al., Localization of a constitutively active, phagocyte-like NADPH oxidase in rabbit aortic adventitia: enhancement by angiotensin II, Proc. Natl. Acad. Sci. USA. December 23; 94(26):14483-8 (1997), incorporated herein by reference as if set forth in its entirety, and used to visualize collagen secretion into growth media. These cells were transfected with green fluorescent protein (GFP) and SMAD3 adenoviral vectors expressing Smad3 (AdSmad3) and GFP (AdGFP), constructed as previously described in Ryer, E. et al., Arterioscler Thromb Vasc Biol. 26:780-786, 2006, incorporated herein by reference as if set forth in its entirety. Adenoviral vector expressing GFP was used as a control (AdGFP).

Immunoblotting Analysis.

Collagen produced by rat fibroblasts was measured using Western blotting. Conditioned medium (CM) obtained from SMCs was added to rat fibroblasts. Collagens III and I in culture medium from the rat fibroblasts treated with SMC-conditioned medium was quantified following 3 days (72 hours) of rat fibroblast growth.

GFP (control) and Smad3-transfected SMCs were starved for 24 hours in 0.5% serum DMEM medium and then treated with TGFbeta1 (5 ng/ml) for 48 hours. The conditioned medium from these cells was concentrated and added with serum-free medium to rat fibroblasts which had been starved for 24 hours using 0.5% serum medium. Culture medium from CM-treated rat fibroblasts was collected following 72 hours of treatment and collagens III and I in the medium was quantified by Western blotting. Thirty micrograms of proteins from each sample were separated on 10% SDS-PAGE gels. Protein samples were transferred to a polyvinylidene fluoride (PVDF) membrane. Rabbit anti-collagen type III (1:1000) and I (1:1000) (Fitzgerald) and goat-anti Rabbit (1:5000) were used as primary and secondary antibodies respectively to confirm immunoblotting. Conditioned medium was blotted parallel to unconditioned culture medium to rule out the possibility of presence of collagen in the former.

Immunoblotting was carried out to visualize collagen I and III in culture medium after treating rat fibroblasts with CTGF (0.1 µg/ml) and IGF-2 (0.3 µg/ml) for 72 hours. These experiments were replicated using insulin in place of IGF-2.

Enzyme Linked Immunosorbent Assay (ELISA).

ELISA was used to detect the presence of IGF-2 and CTGF in the conditioned medium using the primary antibodies from Abcam® according to manufacturer's instructions. Fitzgerald Collagen I and III primary antibodies were used to visualize changes in collagen production in the fibroblast culture medium following treatment with CTGF and IGF small interfering RNA-(siRNA) transfected conditioned medium for 72 hours. Goat anti-rabbit secondary antibody (1:200) was used to detect the presence of IGF, CTGF and collagen in the conditioned medium and the culture medium respectively.

Small Interfering RNA Transfection.

Transfection of cultured aortic SMCs was performed using Lipofectamine™ RNAiMAX reagent according to the manufacturer's instructions. Confirmation of siRNA effectiveness in decreasing CTGF and IGF-2 expression was confirmed with ELISA.

MTT Cell Proliferation Assay.

MTT cell proliferation assay was performed to visualize the effect of insulin on SMC proliferation. Smad3-transfected rat SMCs were stimulated with TGF-beta. Cells were then treated with 1 μg of insulin and the MTT assay was performed following 96 hours of treatment.

Balloon Injury Model and In Vivo Studies.

In vivo studies conformed to the Guide for the Care and Use of Laboratory Animals published by the US National Institute of Health. Approval from the Institutional Animal Care and Use Committee was granted. Male Sprague-Dawley rats underwent angioplasty of the left common carotid artery. Periadventitial Insulin (1 microgram) along with CTGF (100 nanogram) suspended in 200 μL of Pluronic® gel was applied to the adventitial surface of the artery immediately after injury. Control animals were subjected to application of Pluronic® gel only. Fourteen days after injury, carotid was harvested utilizing perfusion fixation at physiological pressure of 100 mmHg.

Morphometric Analysis.

Paraffin-embedded arteries were cut into 5 μm sections for analysis. Morphometric analysis was carried out on arteries stained with Haematoxilin and Eosin. For each animal, 10 sections were selected for analysis using digital software for Dell PC Computers (ImageJ and Photoshop V.7). The areas encompassed by the lumen surface (luminal area), internal elastic lamina-lumen surface (luminal area), internal elastic lamina-lumen surface (neointimal area), EEL-internal elastic lamina (medial area) and EEL length were measured. For evaluation of remodeling index, the EEL was measured and compared with that of controls.

Statistical Analyses.

Values were expressed as fold increase or mean+/− SE. Student's t-test was used to compare the results.

Example 2

TGFbeta and Smad3 Stimulation Increases Production of Collagen III Relative to Collagen I in Rat Aortic Fibroblasts Endogenous Smad3 expression is upregulated following injury (Tsai, Hollenbeck et al., 2009). Smad3 gene transfer can lead to increased total collagen synthesis and adaptive vessel remodeling (Kundi, Hollenbeck et al., 2009). However, increased collagen is also associated with constrictive remodeling (Kundi, Hollenbeck et al., 2009). In view of these conflicting reports, the inventors predicted that the relative difference in the form of collagen produced (i.e., type I relative to type III) might responsible for responses of vessel expansion/constriction following injury.

To stimulate collagen production by fibroblasts in vitro, Smad3-transfected SMCs were starved in 0.5% serum and then treated with TGF-beta (5 ng/ml) for 48 hours to generate TGF-beta-treated Smad3-transfected SMC CM. The CM obtained from this culture was then added to rat aortic fibroblasts. Medium obtained from CM-treated rat fibroblasts following 3 days in culture was analyzed for collagen III and I. Collagen-III secretion from the fibroblasts increased 2.7±0.43 fold ($p<0.05$), while collagen-I increased only 1.4±0.06 fold ($p<0.05$) in response to the addition of the CM (FIG. 1A) relative to untreated cells. These results confirmed that the composition of total collagen produced by aortic adventitial fibroblasts is influenced by the products secreted by SMCs.

Example 3

TGFbeta/Smad3-Treatment Causes SMCs to Increase CTGF and IGF-2 Production

Medial SMCs can influence adventitial fibroblast behavior through a TGFbeta/Smad3 dependent soluble factor (Kundi et al., 2009). This factor might be CTGF, previously demonstrated to stimulate myofibroblast transformation, proliferation and collagen production (Blom et al. 2002; Kundi et al. 2009). CTGF has an Insulin-Like Growth Factor (IGF) domain. Further, the presence or absence of other growth factors such as IGF-2 determines the biological response of the target cell (Gore-Hyer, Pannu et al. 2003; Grotendorst, Rahmanie et al. 2004; Grotendorst and Duncan 2005).

Figure 2:
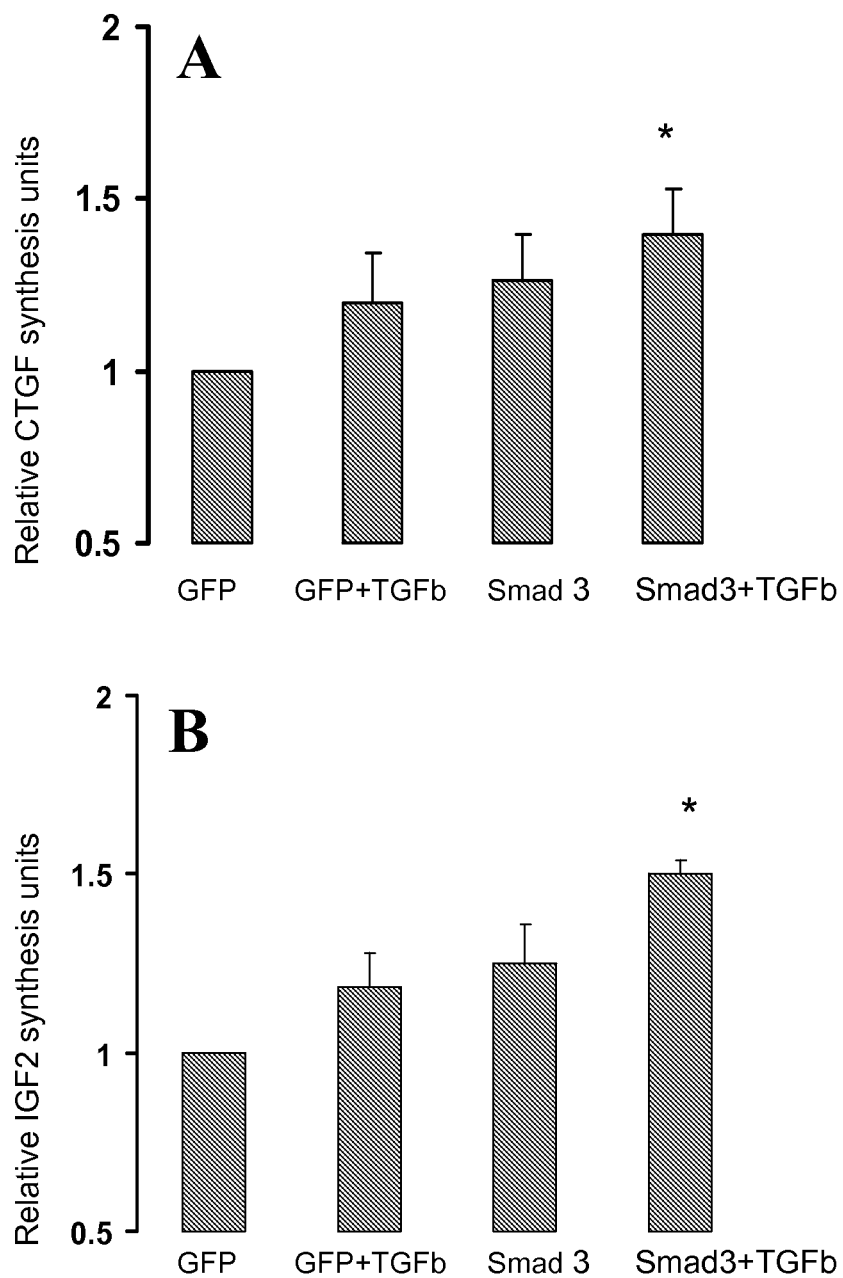
FIGS. 2A-B illustrate the presence of CTGF and IGF-2 in conditioned medium derived from Smad3 over-expressing SMCs. (A) Direct ELISA depicting CTGF in the respective conditioned media from SMCs ($*p<0.05$). (B) Direct ELISA depicting IGF-2 in the respective conditioned media from SMCs ($*p<0.05$).

CTGF and IGF-2 are present in the CM derived from SMCs that overexpress Smad3 (FIGS. 2A and B respectively). Further, an mRNA expression array analysis conducted by the inventors showed an increase in CTGF and IGF-2 mRNA production by TGFbeta/Smad3-treated SMCs following 48 hours of treatment. IGF-2BP3 was found to be increased 2.8 and 2.4 folds following 6- and 48 hours treatment respectively (data not shown). IGF-2 has been shown to interact with CTGF through an IGF-binding domain and to increase matrix protein synthesis (Grotendorst, Rahmanie et al., 2004; Grotendorst and Duncan, 2005).

Example 4

SMCs Influence Fibroblast Function Through CTGF and IGF-2

Figure 3:
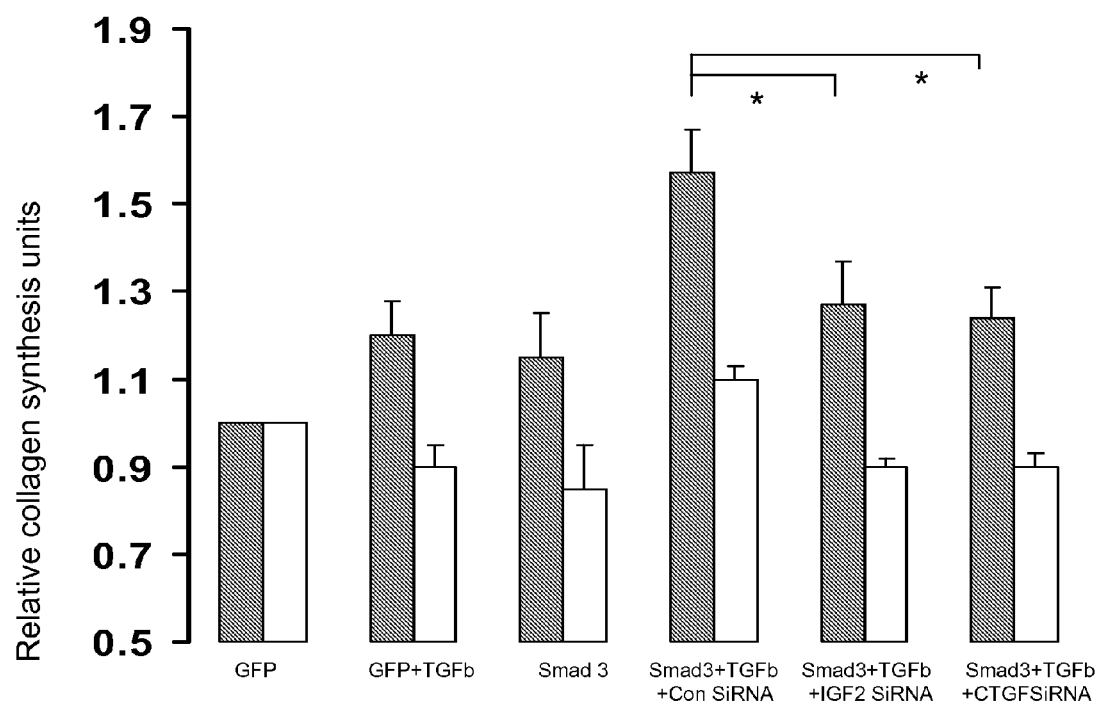
FIG. 3 illustrates that both CTGF- and IGF-2 siRNAs inhibit Smad3-infected SMCs from conditioning media that stimulate collagen III synthesis.
Figure 4:
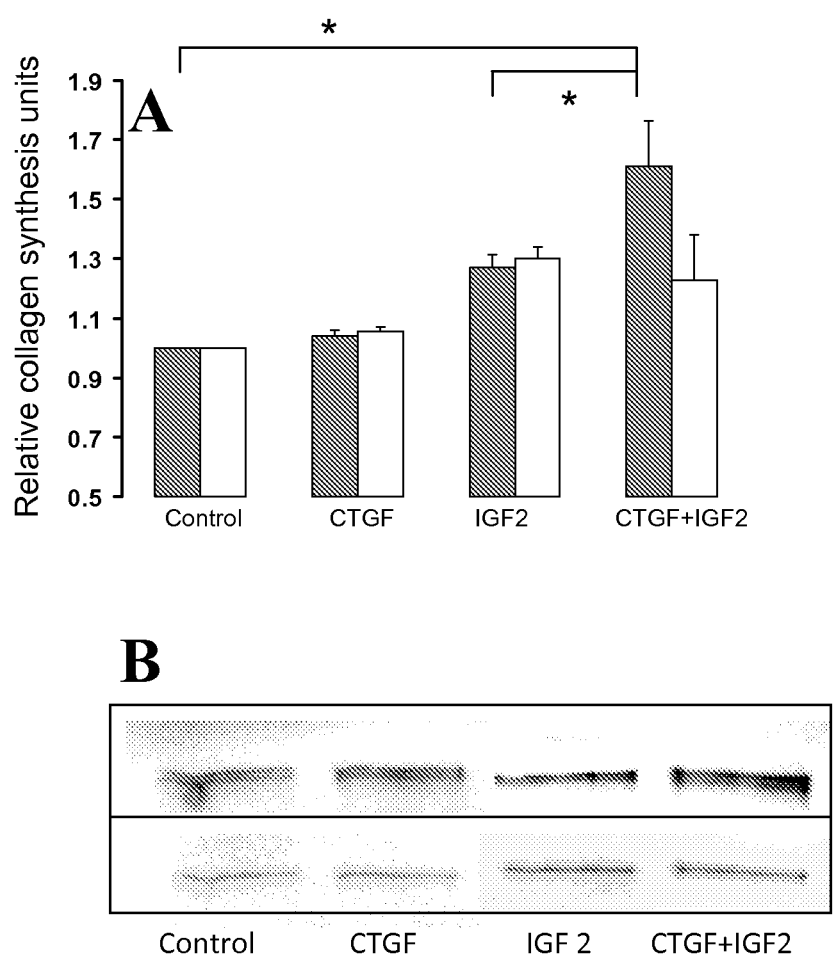
FIG. 4 illustrates that recombinant CTGF in combination with recombinant IGF-2 mirror the effect of Smad3+TGF-beta-treated SMC-conditioned medium on collagen III production by fibroblasts. (A) Direct ELISA indicating collagen III (dark) and collagen I (light) in culture medium following treatment of rat aortic fibroblasts with CTGF, IGF, CTGF and IGF for 72 hours ($*p<0.05$). (B) Western blot for collagen III and I of the culture medium describe in FIG. 4, part A.

To demonstrate the role of CTGF and IGF-2 in collagen production, the inventors used siRNA to block production of CTGF and IGF-2 in SMCs. Compared with the scrambled control, siRNAs reduced CTGF and IGF-2 production by SMCs relative to untreated cells. Both CTGF- and IGF-2 siRNAs blocked the ability of Smad3-infected SMCs to condition media that stimulated fibroblast collagen III synthesis (FIG. 3). Further, in vitro fibroblast studies showed that recombinant CTGF along with IGF-2 mimicked the effect of Smad3+TGFbeta-treated SMC-conditioned medium, increasing collagen III production two times as compared to the control ($p<0.05$) (FIG. 4). Fibroblast synthesis of collagen I was not altered significantly by treatment with recombinant CTGF and IGF-2 (FIG. 4).

Example 5

CTGF and Collagen Production

Figure 5:
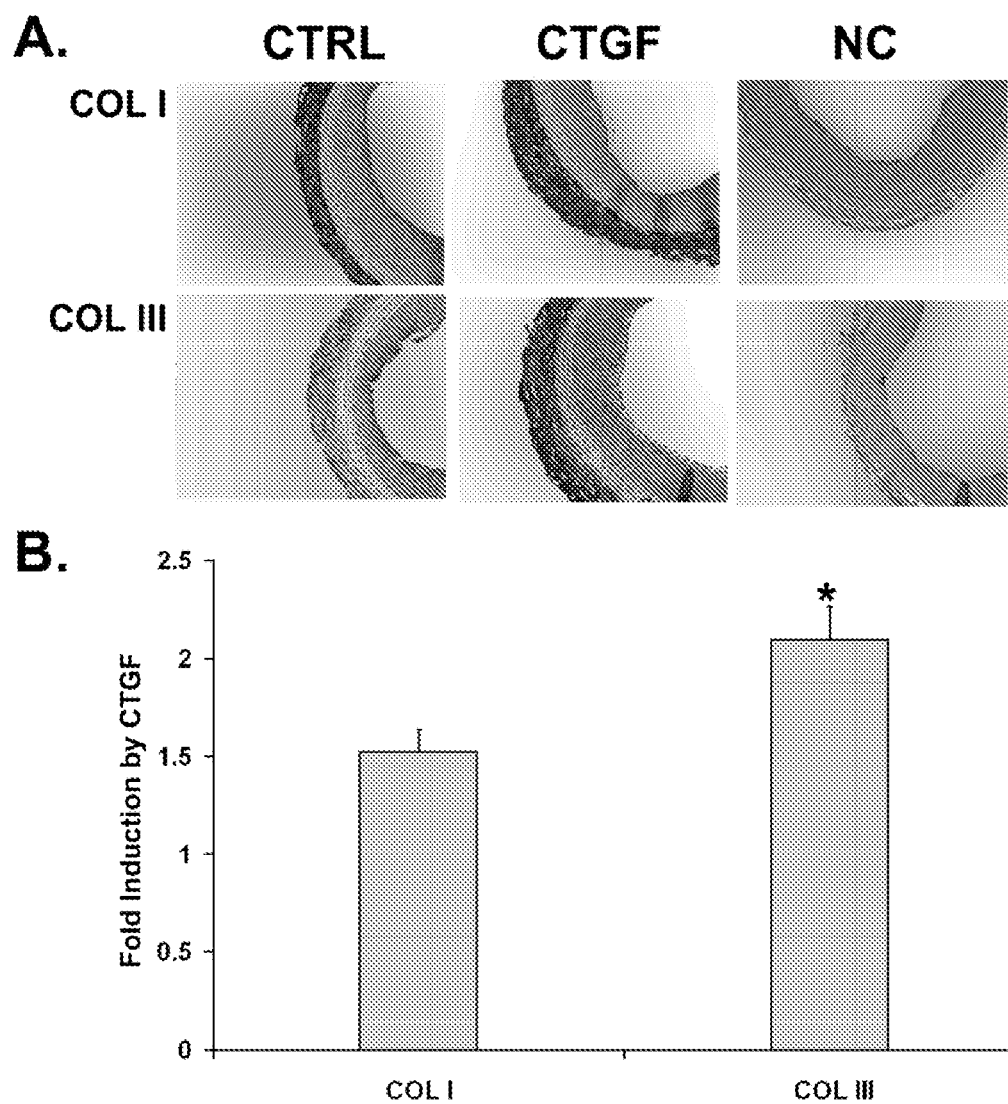
FIG. 5 illustrates collagen subtype induction by CTGF in vivo. Arteries were injured and treated with recombinant CTGF as described in FIG. 2. Arterial sections, harvested at 14 days post-injury, were subsequently immunostained for either Type I (COLI) or Type III collagen (COLIII). (A) Representative tissue sections from solvent-(CTRL) or CTGF-treated arteries (CTGF). Negative controls were established by staining sections without primary antibodies to collagen. 100X (B) Semi-quantification of adventitial COLI or COLIII was carried out, and the effects of CTGF on COLI or COLIII were expressed as fold induction; $n=6$, $*p<0.05$ as compared to COLIII.

FIG. 5A shows staining for collagens III and I, 14 days after carotid artery injury and perivascular application of CTGF (at 80 ng in 200 microliters of Pluronic® gel) to the injured vessel. FIG. 5B depicts CTGF-mediated differential production of collagens III and I when CTGF was applied around a balloon-injured vessel. The amount of collagen III increased significantly more as compared to collagen I.

Example 6

Figure 6:
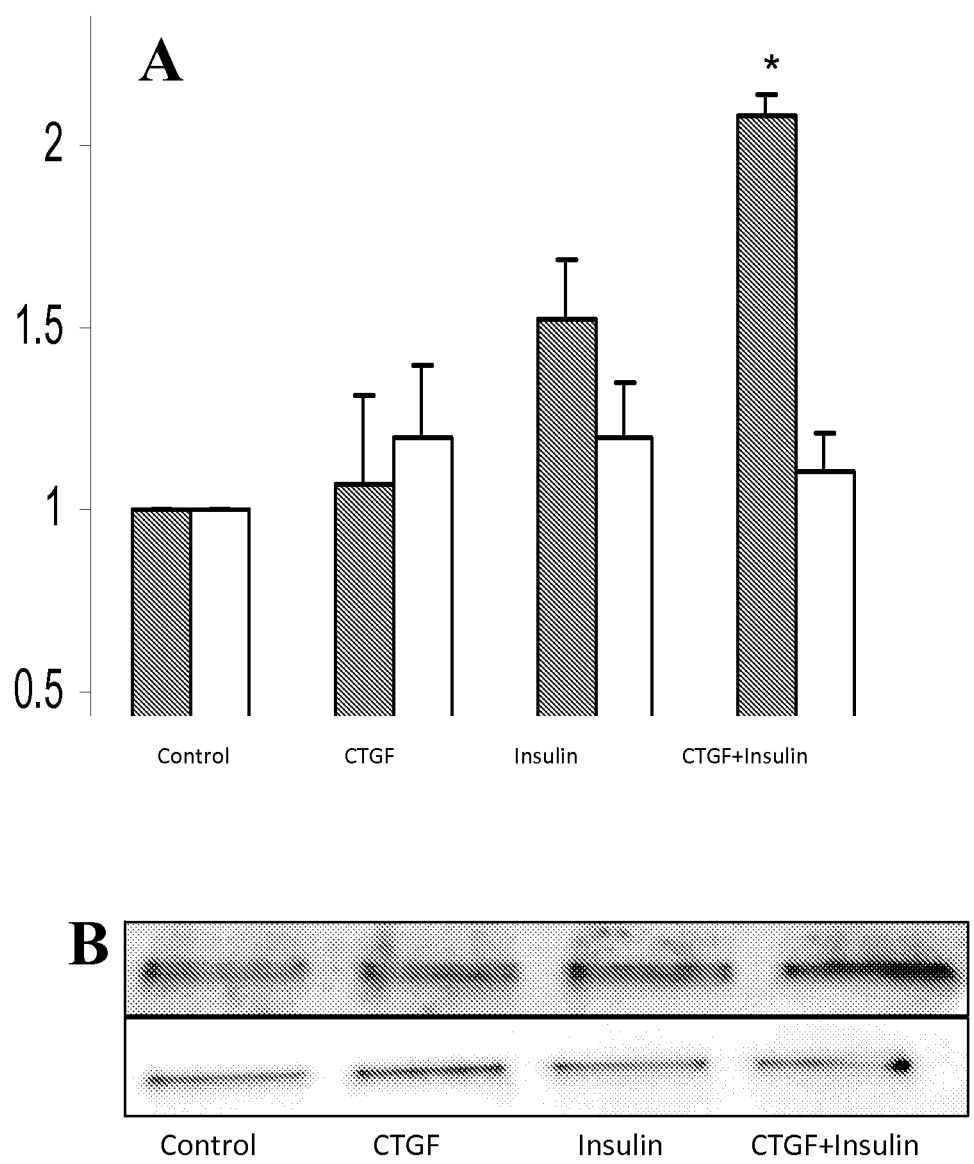
FIG. 6 illustrates that insulin can replace IGF-2 as an inducer of collagen production in rat aortic fibroblasts. (A) Direct ELISA indicating collagen III (dark) and collagen I (light) in culture medium following treatment of rat aortic fibroblasts with CTGF, insulin, CTGF and insulin for 72 hours ($*p<0.05$). (B) Western blot for collagen III and I of the culture medium described in FIG. 6A.

Insulin can Replace IGF-2 as an Inducer of Collagen Production by Rat Aortic Fibroblasts Insulin and IGF-2 are structurally similar. Advantageously, insulin is already approved for medical use by the FDA. To determine whether insulin induce collagen III production in rat aortic fibroblasts, the inventors repeated the experiments described in Example 4 using insulin (1 ug) and CTGF to treat fibroblasts instead of IGF-2 and CTGF. Like IGF-2, insulin in combination with CTGF synergistically increased collagen III production from rat aortic fibroblasts relative to collagen I (FIG. 6).

Example 7

Insulin Decreases Smad3-Stimulate SMC Proliferation

Figure 7:
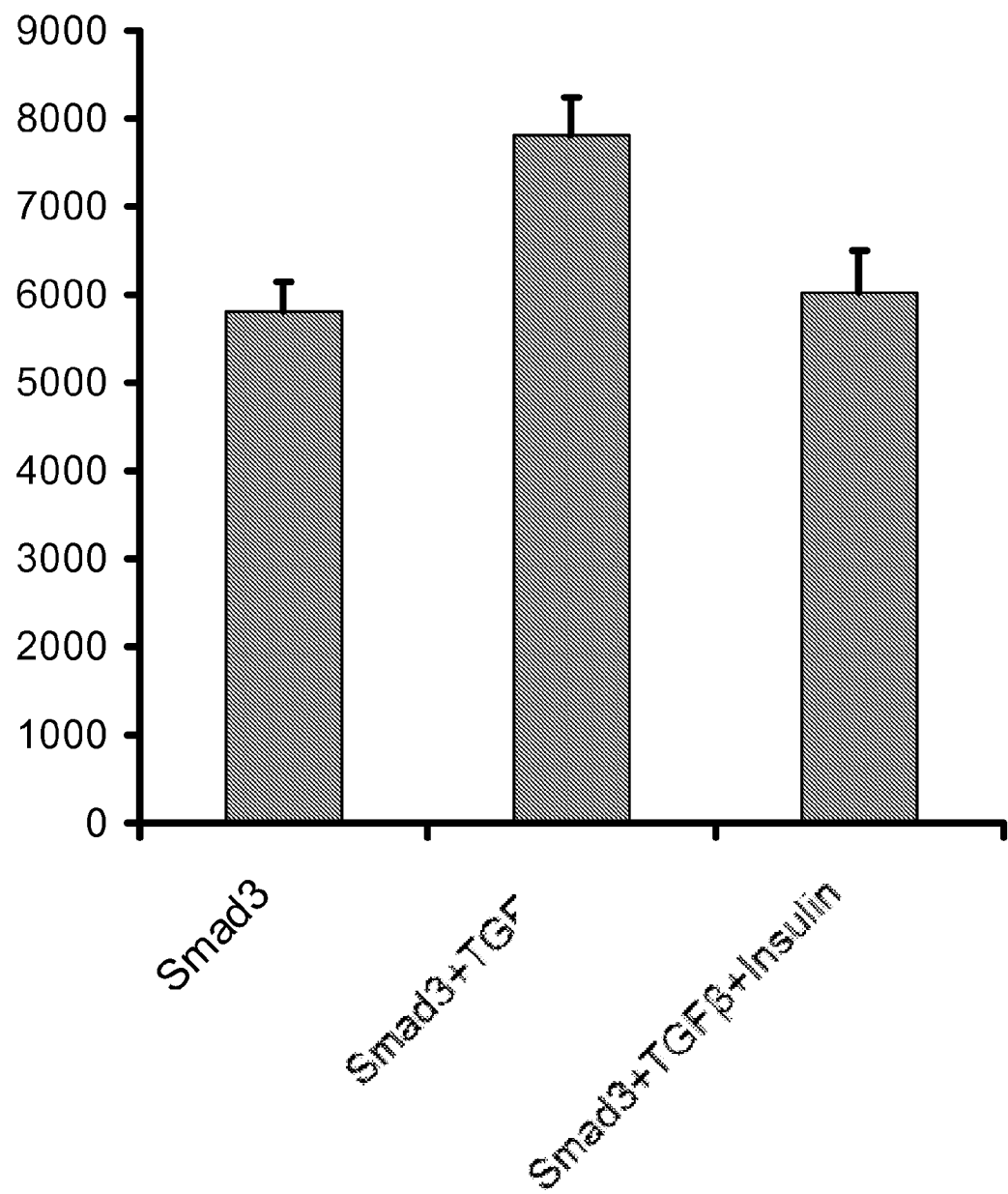
FIG. 7 illustrates a MTT proliferation assay of Smad3-expressing smooth muscle cells (SMCs) at 96 hours after treatment with TGF-beta (5 ng/ml) or TGF beta (5 ng/ml)+ Insulin (1 μg/ml).

To determine whether insulin is sufficient for decreasing TGF-beta and Smad3-stimulated SMC proliferation, an MTT proliferation assay was carried out. Insulin abolished the TGF-beta-stimulated proliferation of Smad3-expressing SMCs (FIG. 7).

Example 8

Figure 8:
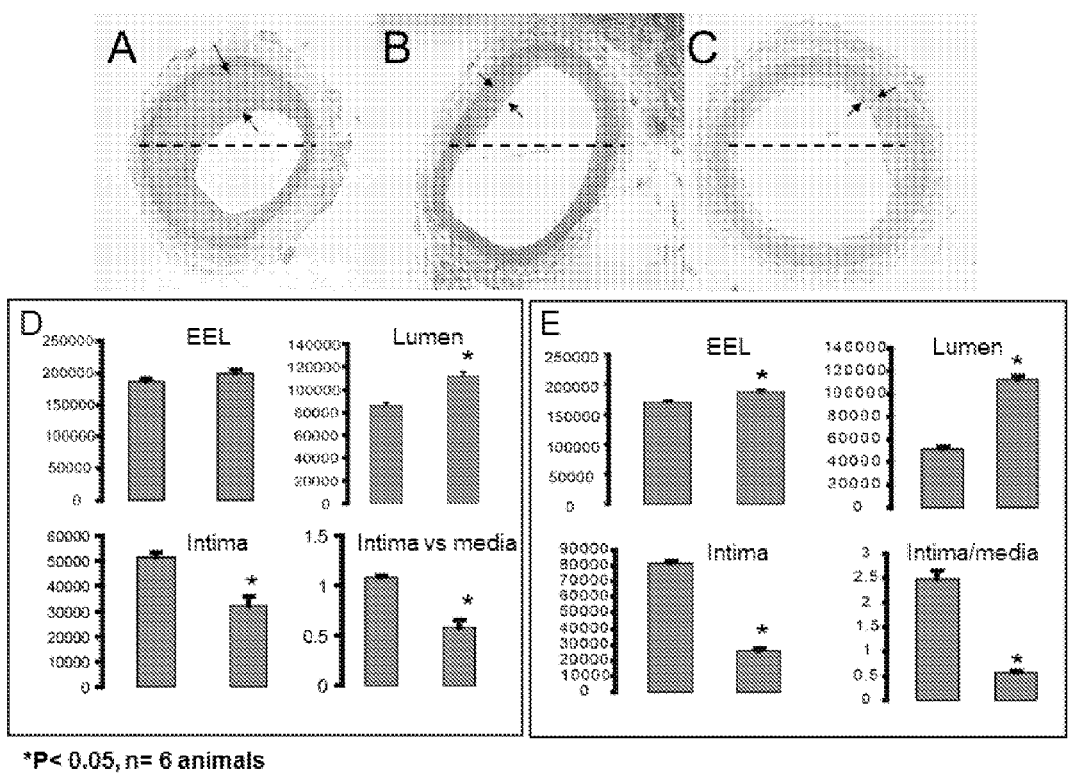
FIG. 8 illustrates in vivo studies of rat restenosis models treated with using CTGF and insulin. (A) Representative image of control artery treated with 200 μl Pluronic® gel. (B) Injured artery was treated with 1μg insulin in 200 μl Pluronic® gel. (C) Injured artery with 1 μg insulin and 200 ng CTGF treatment in 200 μl Pluronic® gel. (D) Quantitative measurements of the external elastic lamina (EEL) area, Luminal area (Lumen), Intimal area (intima), and intima v/s media ratio for insulin treated arteries and CTGF+Insulin treated arteries (E). The arrows represent the thickness of the intimal layer and the dashed line represents the cross sectional diameter of the untreated vessel.

CTGF and Insulin can Decrease Neo-Intimal Cell Growth and Increase Lumen Size in Rat Carotid Arteries To determine whether a combination of CTGF and insulin can be more effective in producing luminal expansion in vivo, male rats were subjected to left carotid artery balloon angioplasty. Immediately following catheter removal, a combination of CTGF and insulin (or insulin alone) suspended in a Pluronic® gel was applied to the outside of the arterial wall at the site of injury. The rats were sacrificed after 14 days of treatment and carotid artery sections were analyzed for the external elastic lamina (EEL) area, Luminal area (Lumen), Intimal area (intima) and intima vs media ratio (FIG. 8). While treated rat vessels all showed decreased neo-intimal growth and enlarged lumen relative to non-treated vessels, the vessels treated with CTGF+insulin showed increased EEL area as well, producing a greater increase in lumen size (120.16%) compared to the increase of lumen size in the vessels treated with insulin alone (29.24%).

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method of preventing restenosis, the method comprising:
    contacting to an external surface of a blood vessel having an intravascular wound a gel or semi-solid composition comprising connective tissue growth factor (CTGF) and insulin in therapeutically effective amounts to prevent restenosis, wherein the composition suppresses neo-intimal growth and increases adaptive remodeling in the vessel relative to a blood vessel having an intravascular wound that is not contacted to the composition whereby restenosis is prevented, and wherein an effective amount of insulin is about 0.3 µg/mL to about 5 µg/mL, and an effective amount of CTGF is about 0.1 µg/mL to about 0.5 µg/mL.

2. The method of claim 1, whereby the composition increases collagen III synthesis in the contacted vessel relative to a level of collagen I synthesis in the contacted vessel or in the uncontacted vessel.

3. The method of claim 1, wherein the composition is contacted to the blood vessel having an intravascular wound as a wrap.

4. The method of claim 3, wherein the wrap is a perivascular wrap.

5. The method of claim 3, wherein the wrap releases the composition onto the contacted vessel over a period of months.

6. The method of claim 5, wherein the wrap is a perivascular wrap.

7. A gel or semi-solid composition comprising insulin and connective tissue growth factor (CTGF) in therapeutically effective amounts to treat restenosis, wherein an effective amount of insulin is about 0.3 µg/mL to about 5 µg/mL, and an effective amount of CTGF is about 0.1 µg/mL to about 0.5 µg/mL.

8. A gel or semi-solid composition comprising insulin and CTGF in therapeutically effective amounts to prevent restenosis, wherein an effective amount of insulin is about 0.3 µg/mL to about 5 µg/mL, and an effective amount of CTGF is about 0.1 µg/mL to about 0.5 µg/mL.

9. A perivascular wrap for preventing restenosis, comprising:
    (a) a substrate adapted for placement on an external surface of a blood vessel having an intravascular at a perivascular wound; and
    (b) a composition supported by the substrate, the composition comprising CTGF and insulin in effective amounts to prevent restenosis of the blood vessel having the intravascular wound, wherein an effective amount of insulin is about 0.3 µg/mL to about 5 µg/mL, and an effective amount of CTGF is about 0.1 µg/mL to about 0.5 µg/mL.

10. The perivascular wrap of claim 9, wherein the substrate comprises a material selected from a polymeric material and a hydrogel material.

11. A perivascular wrap for treating restenosis, comprising:
    (a) a substrate adapted for placement on an external surface of a blood vessel having an intravascular wound; and
    (b) a composition supported by the substrate, the composition comprising CTGF and insulin in effective amounts to treat restenosis of the blood vessel having the intravascular wound, wherein an effective amount of insulin is about 0.3 µg/mL to about 5 µg/mL, and an effective amount of CTGF is about 0.1 µg/mL to about 0.5 µg/mL.

12. The perivascular wrap of claim 11, wherein the substrate comprises a material selected from a polymeric material and a hydrogel material.

* * * * *

UNITED STATES PATENT AND TRADEMARK OFFICE
CERTIFICATE OF CORRECTION

| | | Page 1 of 1 |
|---|---|---|
| PATENT NO. | : 9,132,171 B2 | |
| APPLICATION NO. | : 13/795235 | |
| DATED | : September 15, 2015 | |
| INVENTOR(S) | : Shakti Goel et al. | |

It is certified that error appears in the above-identified patent and that said Letters Patent is hereby corrected as shown below:

In The Specification

Column 9, line 59  -  "preventing" should be --reducing the incidence of--

Column 10, line 6  -  "restenosis is prevented" should be --the incidence of restenosis is reduced--

Column 10, line 31  -  "prevent" should be --reduce the incidence of--

Column 10, line 35  -  "preventing" should be --reducing the incidence of--

Column 10, line 42  -  "prevent" should be --reduce the incidence of--

Signed and Sealed this
Ninth Day of February, 2016

Michelle K. Lee
*Director of the United States Patent and Trademark Office*